(12) United States Patent
Cutrer

(10) Patent No.: US 6,503,186 B1
(45) Date of Patent: *Jan. 7, 2003

(54) RADIOACTIVE SEED WITH MULTIPLE MARKERS AND METHOD FOR USING SAME

(75) Inventor: L. Michael Cutrer, Chatsworth, CA (US)

(73) Assignee: North American Scientific, Inc., Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/280,097

(22) Filed: Mar. 29, 1999

Related U.S. Application Data

(63) Continuation-in-part of application No. 08/904,695, filed on Aug. 1, 1997, now abandoned.

(51) Int. Cl.[7] .......................... A61N 5/00; A61M 36/00
(52) U.S. Cl. .......................................................... 600/8
(58) Field of Search ............................................. 600/1–8

(56) References Cited

U.S. PATENT DOCUMENTS

| | | | | |
|---|---|---|---|---|
| 3,351,049 A | * | 11/1967 | Lawrence | 600/7 |
| 4,323,055 A | * | 4/1982 | Kubiatowicz | 600/7 |
| 4,784,116 A | * | 11/1988 | Russell, Jr. et al. | 600/7 |
| 5,242,373 A | * | 9/1993 | Scott et al. | 600/7 |
| 5,683,345 A | * | 11/1997 | Waksman et al. | 600/3 |
| 5,997,463 A | * | 12/1999 | Cutrer | 606/8 |
| 6,132,359 A | | 10/2000 | Bolenbaugh | |

FOREIGN PATENT DOCUMENTS

| | | |
|---|---|---|
| WO | 9719706 | 6/1997 |
| WO | 9922812 | 5/1999 |
| WO | 9940970 | 8/1999 |
| WO | 0059571 | 10/2000 |

* cited by examiner

*Primary Examiner*—John P. Lacyk
(74) *Attorney, Agent, or Firm*—Pillsbury Winthrop LLP

(57) ABSTRACT

A radioactive seed which discloses the orientation and the location of the seed when the seed is exposed to X-ray photography is provided. The seed contains multiple X-ray detectable markers which will disclose the orientation and the location of the seed when the seed is exposed to X-ray photography. The seed can also have a single marker which wraps around the external surface of the seed or wraps around a carrier body within the seed. The single marker will also disclose the orientation as well as the location of the seed.

5 Claims, 7 Drawing Sheets

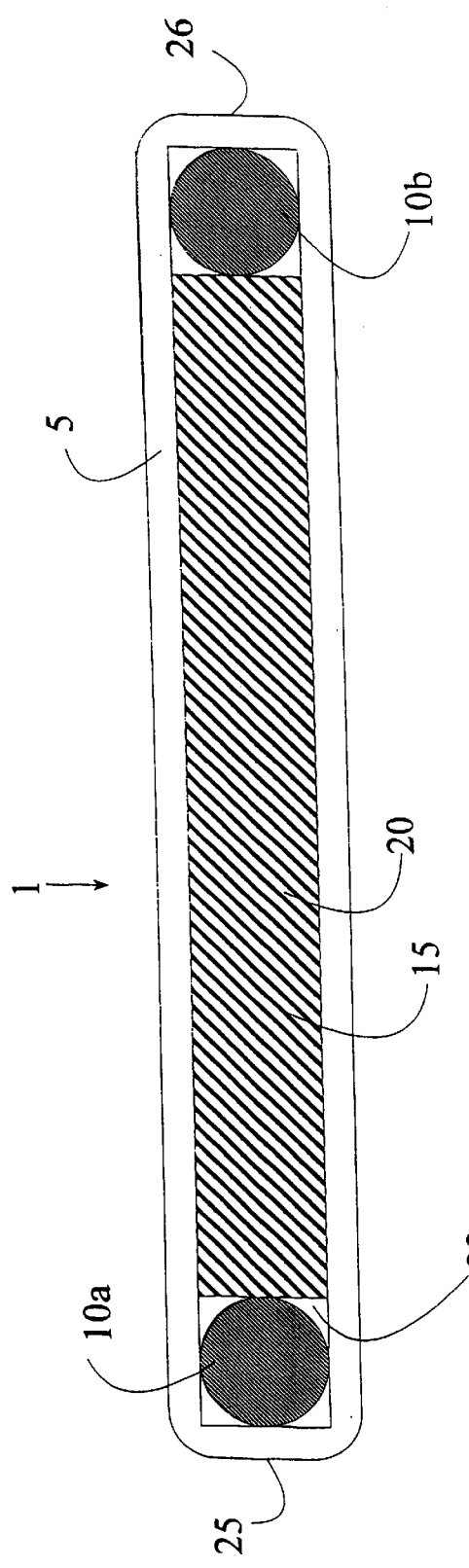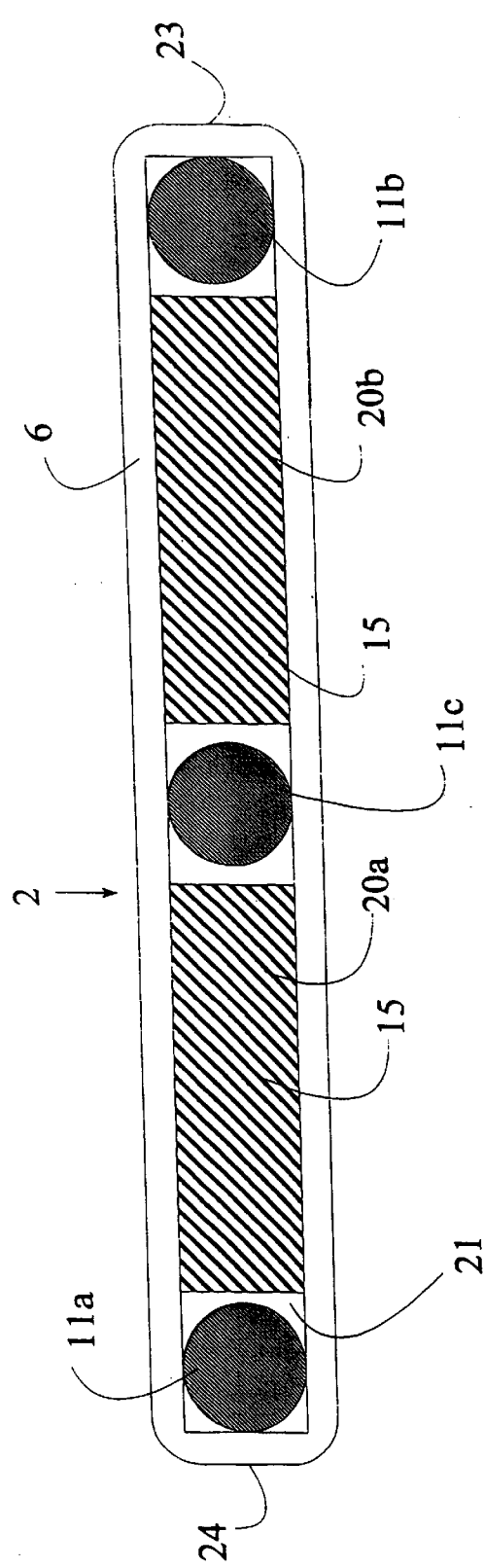

RADIOACTIVE SEED WITH MULTIPLE MARKERS AND METHOD FOR USING SAME

This application is a continuation-in-part application of application Ser. No. 08/904,695, filed Aug. 1, 1997 now abandoned.

FIELD OF THE INVENTION

This invention relates to radioactive seeds and, in particular embodiments, to improved radioactive seeds for treating diseased tissues with radiation therapy.

BACKGROUND OF THE INVENTION

Over the years, brachytherapy sources implanted into the human body have become a very effective tool in radiation therapy for treating diseased tissues, especially cancerous tissues. The brachytherapy sources are also known as radioactive seeds in the industry. Typically, these radioactive seeds are inserted directly into the tissues to be irradiated using surgical methods or minimally invasive techniques such as hypodermic needles. These radioactive seeds typically contain a radioactive material such as iodine-125 which emits low energy X-rays to irradiate and destroy malignant tissues without causing excessive damage to the surrounding healthy tissue, as disclosed by Lawrence in U.S. Pat. No. 3,351,049 ('049 patent). Because radioactive materials like iodine-125 have a short half-life and emit low energy X-rays, the radioactive seeds can be left in human tissue indefinitely without the need for surgical removal. However, although radioactive seeds do not have to be removed from the embedded tissues, it is necessary to determine the position and the number of radioactive seeds implanted in a patient's tissue to effectively treat the patient. This information is also useful in computing the radiation dosage distribution in the tissue being treated so that effective treatment can be administered.

In the '049 patent, the radioactive seed includes a therapeutic amount of radioisotope appropriately distributed on a carrier body. The carrier body is sealed inside an elongated cavity of a capsule to prevent the radioisotope from interacting with body fluids while at the same time permitting the radiation to pass through the walls of the capsule. Furthermore, to allow X-ray detection of the radioactive seed, the radioactive seed contains an X-ray marker made of a dense, high atomic number material, such as gold, which can block the transmission of X-rays so that the radioactive seed can be detected by using X-ray photographic techniques. The capsule, which is typically made out of a low atomic number material, cannot be detected using X-ray photographic techniques because low atomic number materials allow X-rays and radiation to pass through them, instead of blocking X-rays and radiation.

The '049 patent discloses two methods of providing an X-ray marker. In one method, a small ball constructed of a dense, high atomic number material, such as gold or tungsten, is provided in between two cylindrical carrier bodies impregnated with a radioisotope. In another method, a wire made of a high atomic number dense material is located along the central axis of symmetry of the carrier body that is impregnated with a radioisotope. Both the X-ray marker and the carrier body are encapsulated and sealed within a low atomic numbered material container or a capsule which minimally absorbs the radiation emitted by the radioisotope.

Although the above-described methods of providing an X-ray marker are effective in detecting the radioactive seed, they have certain problems. In the first method in which a small ball is provided as a X-ray marker, the ball just appears as a circular dot on an X-ray film and does not provide any information as to the orientation of the radioactive seed. Since the orientation of the radioactive seed is not known, the radiation dosage distribution cannot be computed accurately. In the second method in which a centrally located wire is provided as an X-ray marker, the orientation of the radioactive seed can be determined. However, the second method presents manufacturing problems, such as positioning the wire centrally at the axis of symmetry, which can raise the cost of manufacturing the radioactive seeds.

In other radioactive seeds such as one disclosed by Kubiatowicz in U.S. Pat. No. 4,323,055 ('055 patent), a long cylindrical rod-like member located centrally within the seed is usually employed as an X-ray marker. In the '055 patent, a silver rod coated with iodine-125 is employed as an X-ray marker. Although such X-ray markers like the silver rod in the '055 patent may disclose the orientation of the seed, the silver rod in the '055 patent is coated with the iodine-125 by performing a complicated chemical process which in turn will complicate the overall manufacturing process and raise the cost of manufacturing. As discussed above, the orientation of the seed can be very important in computing the radiation dosage distribution. Therefore, simpler and more cost effective apparatuses and methods are needed in providing X-ray markers which will disclose the orientation of the radioactive seed when the seed is exposed to X-ray photography.

SUMMARY OF THE DISCLOSURE

It is an object of an embodiment of the present invention to provide an improved radioactive seed for use in radiation therapy, which obviates for practical purposes, the above-mentioned limitations.

It is also an object of an embodiment of the present invention to provide a system for monitoring radioactive dosages in affected tissue in brachytherapy.

It is also an object of an embodiment of the present invention to provide simple and cost effective X-ray detectable markers which will disclose the orientation of the radioactive seed when the seed is exposed to X-ray photography.

According to an embodiment of the present invention, a radioactive seed for use in radiation therapy includes a sealed housing having an internal cavity, at least one carrier body disposed within the cavity for maintaining and distributing a radioisotope along the length of the cavity and a plurality of X-ray detectable markers distributed among the at least one carrier body such that the distribution of the X-ray detectable markers discloses the orientation of the radioactive seed when the seed is exposed to X-ray photography.

In particular embodiments of the present invention, the carrier body comprises a plurality of separate carrier units in which each of the carrier units is impregnated with the radioisotope. The carrier units are evenly distributed along the length of the cavity so that the seed emits substantially uniform radiation around the sealed housing of the seed. However, in alternative embodiments, the carrier units can be concentrated at one end of the seed. In addition, the X-ray detectable markers are distributed among the carrier units so that the markers will disclose the orientation of the seed when the seed is exposed to X-ray photography. Both the X-ray detectable markers and the carrier units preferably have a substantially spherical shape like a ball or a bead so that the markers and carrier units can be easily rolled into the cavity of the housing during the manufacturing process.

In other embodiments of the present invention, the X-ray detectable marker wraps around the carrier body or the sealed housing in a spiral shape to reveal the location and the orientation of the radioactive seed. In other embodiments of the present invention, radioactive seeds have different configurations of X-ray detectable marks for identifying a particular type of radioactive source in the seed or dosage level.

Other features and advantages of the invention will become apparent from the following detailed description, taken in conjunction with the accompanying drawings which illustrate, by way of example, various features of embodiments of the invention.

BRIEF DESCRIPTION OF THE DRAWING

A detailed description of embodiments of the invention will be made with reference to the accompanying drawings, wherein like numerals designate corresponding parts in the several figures.

FIG. 1a is a cross-sectional view of a radioactive seed in accordance with a first embodiment of the present invention.

FIG. 1b is a cross-sectional view of a radioactive seed in accordance with a second embodiment of the present invention.

DETAILED DESCRIPTION OF THE PREFERRED EMBODIMENTS

Figure 2:
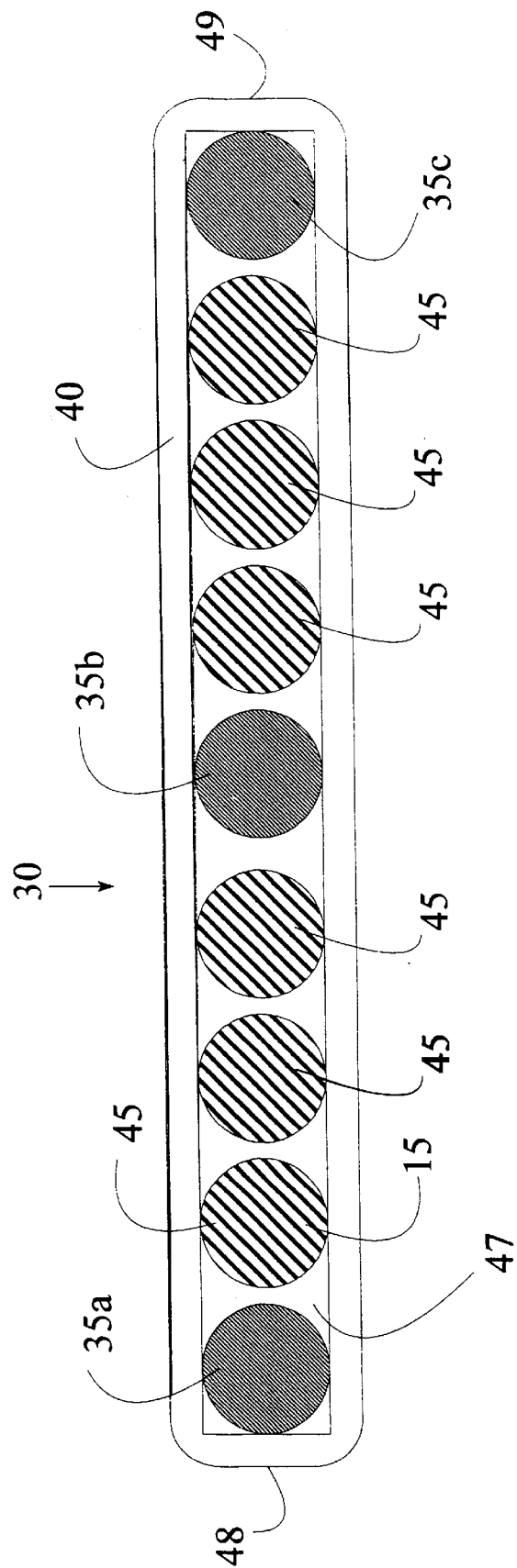
FIG. 2 is a cross-sectional view of a radioactive seed in accordance with a third embodiment of the present invention.

As shown in the drawings for purposes of illustration, the invention is embodied in a radiation seed. In preferred embodiments of the present invention, the radiation seed is used in the human body. However, it will be recognized that further embodiments of the invention may be used in animals or other applications where radiation and markers are required.

Referring to FIG. 1a, a radioactive seed 1 in accordance with a first embodiment of the present invention includes a tubular container or a housing 5 with an internal cavity 22 which contains a therapeutic amount of radioisotope 15 evenly distributed on a carrier body 20 along the length of the cavity 22. In addition, X-ray detectable markers 10a and 10b are disposed at two ends of the carrier body 20, respectively, and the housing 5 is sealed at two ends 25 and 26 to prevent the radioisotope 15 from interacting with body fluids while the seed 1 is implanted within a human tissue.

As shown in FIG. 1, the housing 5 isolates the radioisotope 15 and the X-ray detectable markers 10a and 10b from body fluids by completely encapsulating the radioisotope 15 and the markers 10a and 1b. Therefore, the material for the housing 5 needs to be a non-toxic material that will not interact physically or chemically with body fluids. Otherwise, the housing 5 needs a coating of non-toxic material that will prevent interaction between the housing 5 and body fluids. In addition, the housing 5 should be constructed of a material which will not significantly attenuate the radiation emitted by the radioisotope 15 while having sufficient mechanical strength to allow the implantation of the seed 1 into the human body using hypodermic needles or other appropriate instruments. High atomic number material such as gold or platinum may have sufficient mechanical strength and the requisite nontoxicity, but high atomic number materials like gold will absorb and attenuate a significant amount of radiation emitted by the radioisotope 15 so that effective treatment cannot be administered to a patient. Thus, high atomic number material is not a suitable material for the housing. However, low number atomic metal such as stainless steel or titanium has the requisite nontoxicity, sufficient mechanical strength and the requisite minimal absorption characteristic to prevent significant attenuation of the radiation emitted by the radioisotope 15. In alternative embodiments, medical grade plastics, ceramics, or the like may be used.

Titanium has a high strength-to-weight ratio and a low atomic number, in addition to being exceptionally corrosion resistant and non-toxic. Thus, titanium is a very suitable material for the housing 5. The wall thickness of the titanium may vary from 0.001 of an inch to 0.005 of an inch while the attenuation is about 5–7% per thousandths of an inch for low energy X-rays, such as from iodine-125 or palladium-103, and would be lower for higher energy photons. An optimum value of wall thickness is approximately 0.002 inch. However, smaller or larger thicknesses may be used, with the thickness being dependent on the location of use, the amount of radiation and the type of radioactive material. The ends of the titanium housing can be sealed by using various techniques known in the industry such as laser welding or the like. Such a technique is described in U.S. patent application Ser. No. 09/048,517, entitled "Laser Welded Brachytherapy Source and Method of Making the Same," filed on Mar. 26, 1998, assigned to North American Scientific, Inc., and incorporated herein by reference. In alternative embodiments, the ends may be sealed by a cover secured by adhesives or crimping.

The housing 5 should be preferably designed for implantation using hypodermic needles or other similar instruments designed for implanting the seed 1. As a result, the housing 5 preferably has a long, thin elongated shape with an outer diameter of about 0.5 to 1 millimeter and a length of about 4–5 millimeters to allow the seed 1 to pass through a hypodermic needle. However, smaller or larger diameters may be used, with the diameter being dependent on the location and application in which the seed will be used.

As mentioned above, the housing 5 has an inner cavity 22 which contains a carrier body 20. In preferred embodiments, the carrier body 20 is an ion exchange resin material impregnated with the radioisotope 15. The carrier body 20 is used to concentrate, collect and support the radioisotope 15 so that the radioisotope 15 can be evenly distributed along the length of the cavity 22 to prevent having a point source which can prevent effective treatment. The carrier body 20 generally conforms to the shape of the inner cavity 22 so that the carrier body 20 can be easily inserted into the cavity 22 during the manufacturing process. The carrier body 20 can be constructed from any suitable material that can be impregnated with the radioisotope 15 and that can allow even distribution of the radioisotope 15 along the length of the seed 1. However, the carrier body 20 should be preferably constructed from a low atomic number material since high atomic number material can absorb the radiation from the radioisotope 15. In alternative embodiments, plastics, ceramics, composites, low atomic number metals and the like may be used as carrier bodies.

In preferred embodiments, the material for the radioisotope 15 should be chosen from a material which has a radiation energy in the soft X-ray region, from about 20 to 100 Kev and a half-life of about 5 to 100 days. If the material has a half-life shorter than 5 days, then the material will tend to dissipate before it can be packaged and shipped, and if the material has a half-life longer than 100 days, then the radioactive seed may have to be removed surgically since the seed may emit radiation even after the treatment period is over. Materials such as iodine-125 or palladium-103 can serve as a suitable radioisotope material for the radioisotope 15 since both iodine-125 and palladium-103 have a radiation of approximately 30 Kev energy X-rays and possess a half-life of about 60 days and a half-life of about 10 days, respectively. However, in alternative embodiments, other materials and half-lives may be used, with them being dependent on the treatment period, the radiation intensity needed and the location where the seed 1 will be placed.

In addition to having the carrier body 20 impregnated with radioisotope 15, the cavity 22 also contains a plurality of X-ray detectable markers 10a and 10b. The X-ray detectable markers 10a and 10b are each disposed adjacent to the two ends of the carrier body 20, respectively. However, instead of using just two X-ray detectable markers, more than two X-ray detectable markers may be used. By having two or more X-ray detectable markers, the orientation of the seed 1 can be detected, as well as the location of the seed 1, when the seed 1 is exposed to X-ray photography. Since the X-ray detectable markers 10a and 10b reveal two ends of the seed 1, the orientation of the seed 1 can be determined based upon the locations of the X-ray detectable markers 10a and 10b. In other words, the orientation of the seed 1 can be determined from a line intersecting the X-ray detectable markers 10a and 10b. By disclosing the orientation of the seed 1 in addition to its location, the preferred embodiments of the present invention may also allow for more accurate determination of the radiation dosage distribution in the tissue being treated so that a more effective treatment can be administered. As mentioned above, any multiple number of X-ray detectable markers can be employed to disclose the orientation of the seed 1. For example, instead of just having one marker at each end of the carrier body 20, two markers can be placed adjacent to each end of the carrier body 20.

In preferred embodiments of the present invention, the X-ray detectable markers have a substantially spherical shape like a bead or a ball so that the markers can be easily rolled into the inner cavity 22 to facilitate the manufacturing process and reduce the manufacturing cost. However, in alternative embodiments, other shapes, such as cylinders or the like, may be used so long as manufacturing is not impeded. The X-ray detectable markers are preferably constructed from a dense, high atomic number material, such as gold or tungsten, which will block the transmission of X-rays so that the X-ray detectable markers will appear on an X-ray film used in X-ray photography. However, in alternative embodiments, other materials such as lead or uranium may be used so long as X-rays are blocked and there is no health hazard from their use.

The diameter and the size of the X-ray detectable markers are preferably sufficiently large to allow X-ray detection (i.e., appear on the X-ray film), but the markers are preferably appropriately sized so that the markers would not attenuate the radiation emitted by the radioisotope 15. If a large amount of dense, high atomic number material is used as X-ray detectable markers, then the markers would severely attenuate the radiation emitted by the radioisotope and decrease the effectiveness of the seed. However, as seen in FIG. 1, the X-ray detectable markers 10a and 10b are located at two ends of the seed 1 and would absorb only a small amount of the radiation emitted by the radioisotope 15. Since the two markers 10a and 10b are located at two ends of the seed 1, the uniformity of the radiation emitted around the housing 5 of the seed 1 is only slightly affected.

FIG. 1b shows a radioactive seed 2 in accordance with a second embodiment of the present invention. The radioactive seed 2 is similar to the radioactive seed 1 except that the seed 2 has a carrier body divided into two separate portions 20a and 20b. In addition, the seed 2 has another X-ray detectable marker 11c in between the two portions 20a and 20b. Therefore, the seed 2 has three X-ray detectable markers 11a, 11b and 11c. By having a third marker in the middle, the mid-section of the seed 2 can be easily determined, and the seed becomes more readily identifiable.

FIG. 2 shows a radioactive seed 30 in accordance with a third embodiment of the present invention. A radioactive seed 30 has a housing 40, a cavity 47, two ends 48 and 49, and X-ray detectable markers 35a, 35b and 35c which are similar to the housing 6, the cavity 21, the two ends 23 and 24, and the X-ray detectable markers 11a, 11b and 11c shown in the embodiment of FIG. 1b. However, in FIG. 2, instead of having just one carrier body, a carrier body 45 is divided into multiple separate components or units, and each of the separate carrier units is impregnated with the radioisotope 15. Each unit of the carrier body is used to concentrate, collect and support the radioisotope 15 and is distributed substantially evenly along the length of the cavity 47. In preferred embodiments, each carrier body unit is constructed of the same material as the carrier body 20 in the previous embodiment and has a substantially spherical shape like a bead or a ball so that each carrier body unit can be easily rolled into the cavity 47, just like the X-ray detectable markers, to facilitate the manufacturing process. The dimension of each carrier body unit and the number of the carrier body units can be appropriately adjusted according to the dimension of the cavity 47 and according to the desired amount of radiation emitted by the radioactive seed 30. However, as previously mentioned, the carrier body units should be distributed evenly along the length of the cavity 47 to ensure that the seed 30 emits substantially uniform radiation around the housing 40 of the seed.

In addition to having multiple carrier body units, a multiple number of X-ray detectable markers are distributed evenly among the carrier body units to disclose the orientation and the location of the seed 30 when the seed 30 is exposed to X-ray photography. As shown in FIG. 2, the X-ray detectable markers 35a and 35c are disposed adjacent to the two ends 48 and 49 while the marker 35b is disposed in the middle of the cavity 47. The number and the location of the X-ray markers should be adjusted appropriately depending on the circumstances, but there should be at least two markers in the cavity 47 to allow for determination of the orientation of the seed 30, as discussed above.

Figure 3A:
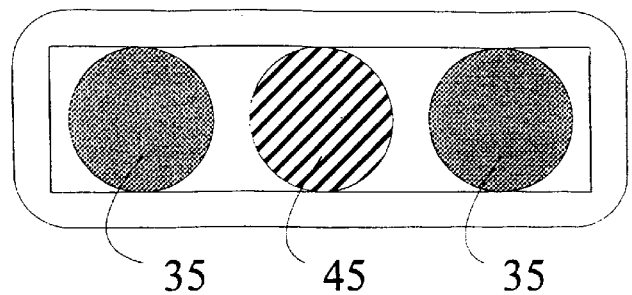
FIG. 3a is a cross-sectional view of a radioactive seed in accordance with a fourth embodiment of the present invention.
Figure 3B:
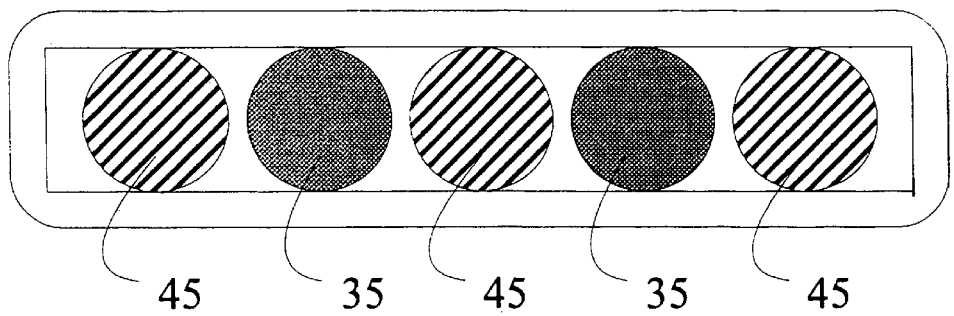
FIG. 3b is a cross-sectional view of a radioactive seed in accordance with a fifth embodiment of the present invention.
Figure 3C:
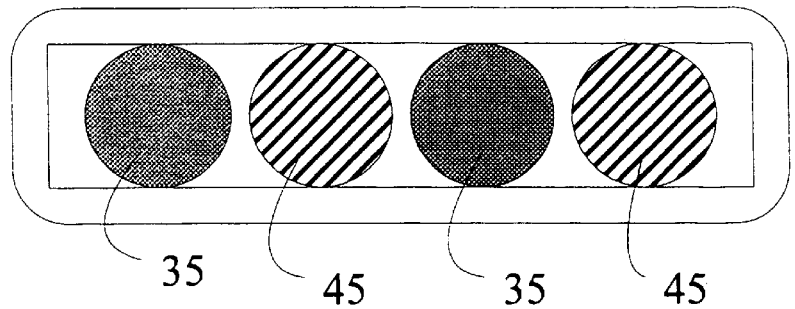
FIG. 3c is a cross-sectional view of a radioactive seed in accordance with a sixth embodiment of the present invention.
Figure 3D:
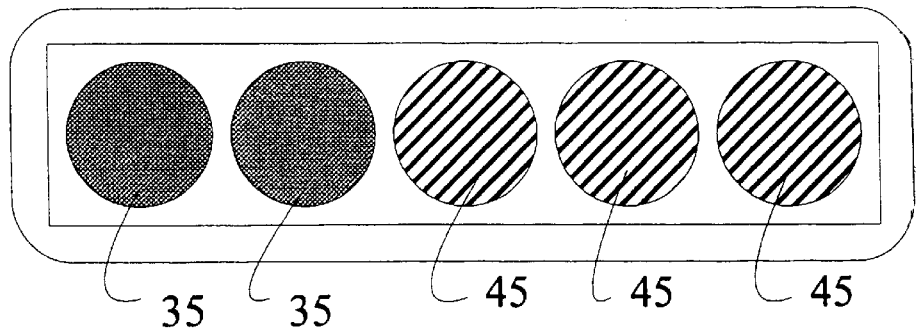
FIG. 3d is a cross-sectional view of a radioactive seed in accordance with a seventh embodiment of the present invention.

FIGS. 3a–3d show various different embodiments of the present invention. Each of the embodiments shown in FIGS. 3a to 3d has a unique arrangement of the carrier body 45 and the Xray detectable markers 35. FIG. 3a shows a radioactive seed smaller than the previous embodiments. The fourth embodiment shown in FIG. 3a has a single unit carrier body with two X-ray detectable markers. FIG. 3b shows a fifth embodiment of a radioactive seed in which the X-ray detectable markers are disposed in between the separate units of the carrier body instead of being placed at the two ends. This facilitates radiation being emitted by the end of the seeds. FIG. 3c shows a sixth embodiment in which there are two X-ray detectable markers and two carrier body units arranged in alternating fashion. FIG. 3d shows a seventh embodiment of a radioactive seed in which the carrier body units are concentrated at one end of the seed instead of being evenly distributed along the length of the inner cavity. Such radioactive seeds can be useful in situations where the radiation has to be concentrated at certain points. Also, the X-ray markers could serve to block radiation in one direction and help minimize radiation effects on healthy tissue. In addition, because the X-ray detectable markers are disposed at the other end of the seed, one end of the seed can be differentiated from the other end when the seed is exposed to X-ray photography.

Figure 4:
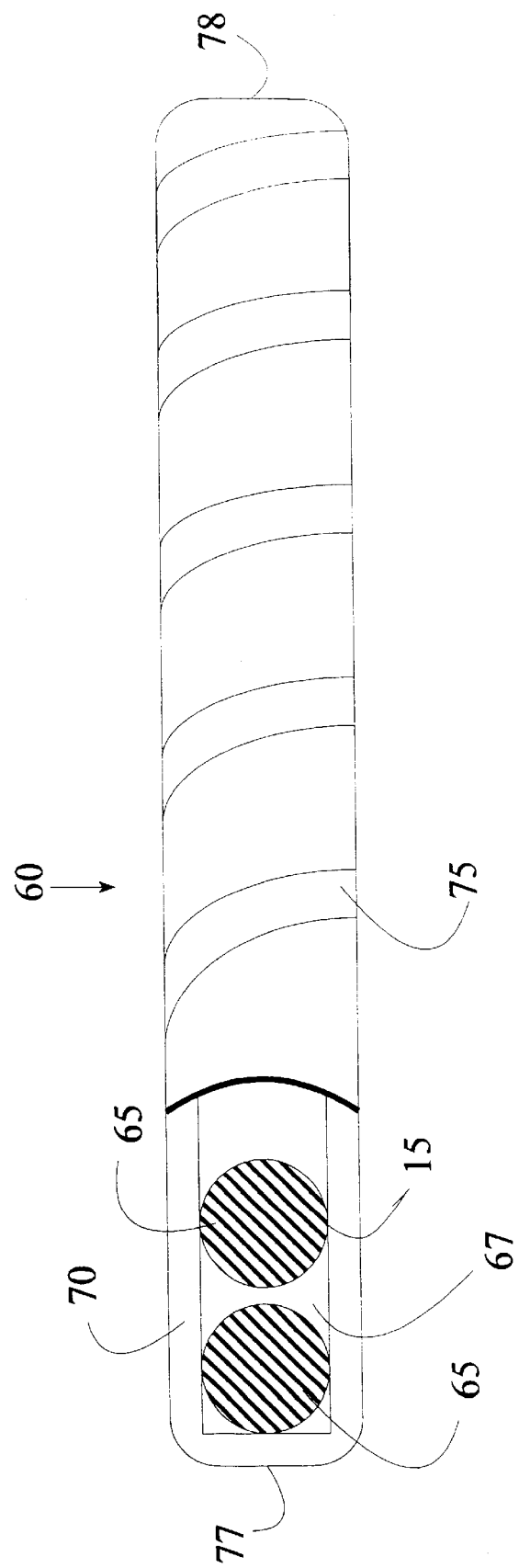
FIG. 4 is a side view with a partial cross-sectional view of a radioactive seed in accordance with a eighth embodiment of the present invention.

FIG. 4 shows an eighth embodiment of the present invention. A radioactive seed 60 shown in FIG. 4 has a housing 70, a cavity 67 and two ends 77 and 78 similar to the ones in the previous embodiments. The seed 60 has a carrier body 65 comprised of multiple separate units similar to the embodiment shown in FIG. 2, but the carrier body 65 may be a single piece similar to the carrier body 20 shown in FIG. 1a. In contrast to the previous embodiments, the seed 60 has an X-ray detectable marker 75 which wraps around the full length of the external surface of the housing 70 like a spiral or a cork screw. Since the marker 75 wraps around the full length of the housing 70, the marker 75 will disclose the orientation of the seed 60 as well as its location when the seed 60 is exposed to X-ray photography. However, the spiral marker still permits radiation to be emitted through the spaces in the spiral or corkscrew. In alternative embodiments, the Xray detectable marker 75 may be formed as an integral part of the housing or placed in the interior of the cavity 67 so long as the X-ray detectable marker 75 will not interfere with manufacturing or placement of the seed.

Figure 5:
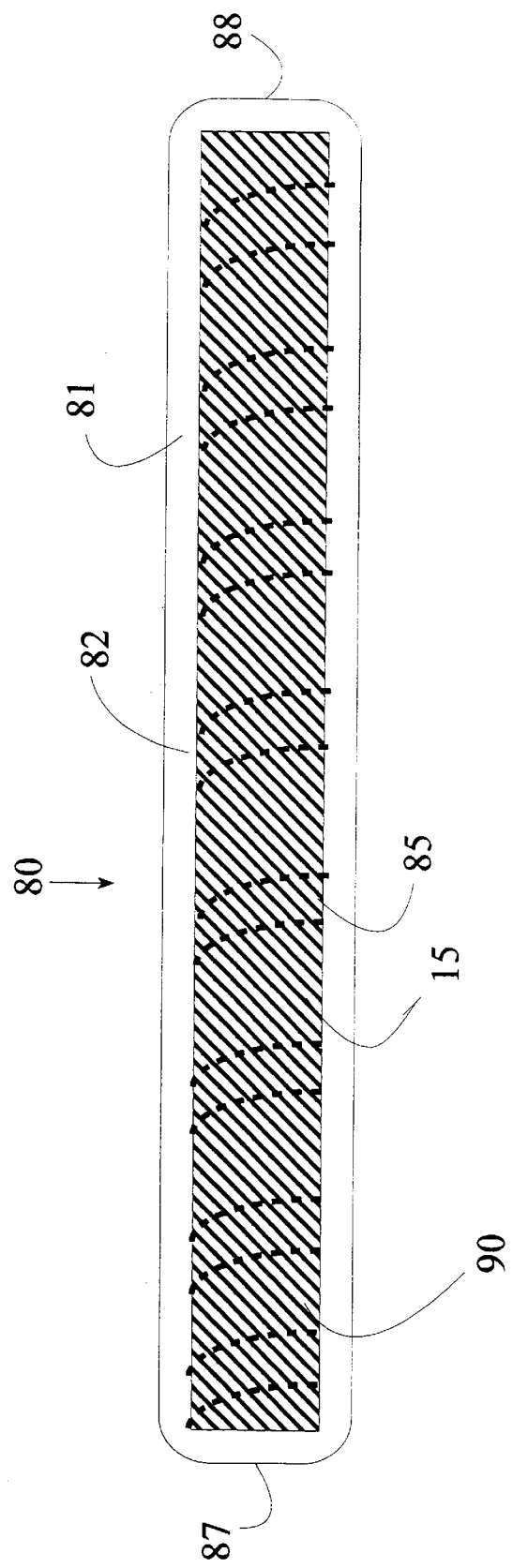
FIG. 5 is a cross-sectional view of a radioactive seed in accordance with a ninth embodiment of the present invention.

FIG. 5 shows a ninth embodiment of the present invention. A radioactive seed 80 has a housing 81, a cavity 82 and two ends 87 and 88 similar to the ones in the previous embodiments. However, the seed 80 has a single carrier body 90 disposed in the cavity 82 and an X-ray detectable marker 85 which wraps around the full length of the carrier body 90 in a spiral shape. Since the marker 85 wraps around the full length of the carrier body 90, the marker 85 will also disclose the orientation of the seed 80 as well as its location when the seed 80 is exposed to X-ray photography.

Figure 6:
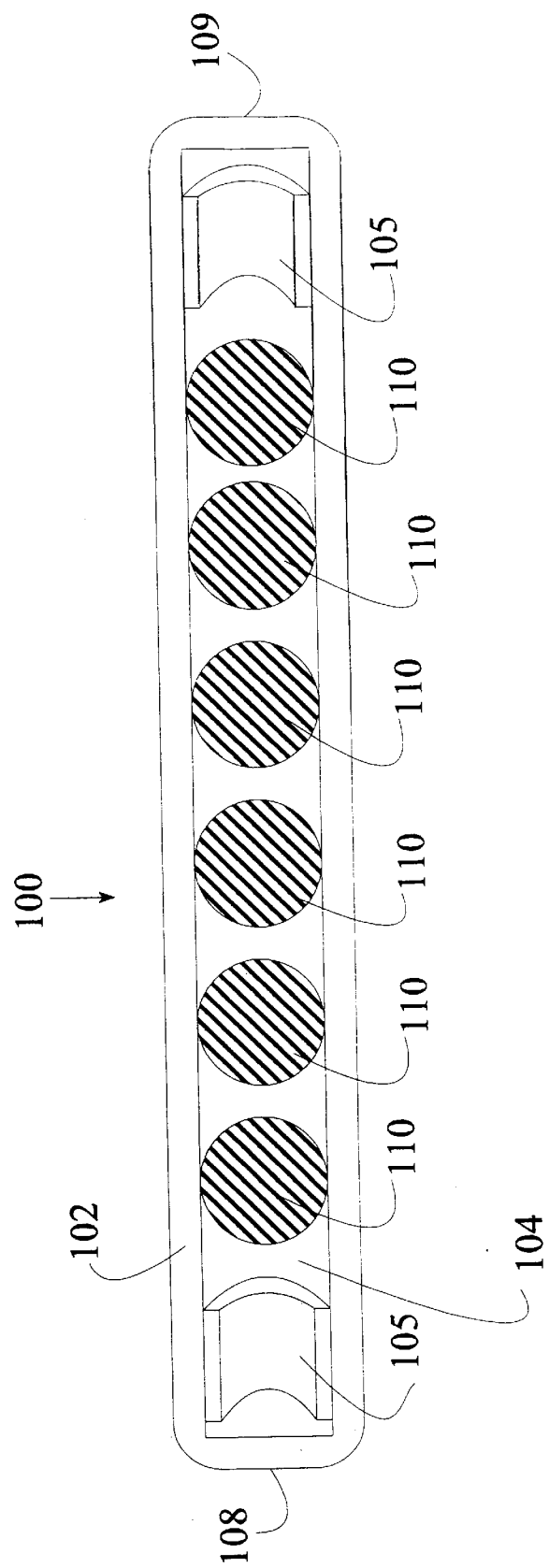
FIG. 6 is a cross-sectional view of a radioactive seed in accordance with a tenth embodiment of the present invention.

FIG. 6 shows a tenth embodiment of the present invention. A radioactive seed 100 has a housing 102, a cavity 104 and two ends 108 and 109 similar to the ones in the previous embodiments. The seed 100 also has a carrier body 110 comprised of multiple separate units similar to the embodiment shown in FIG. 2, but the carrier body 110 may be a single piece similar to the carrier body 20 shown in FIG. 1a. In contrast to the previous embodiments, the seed 100 has X-ray detectable markers 105 which have a substantially cylindrical shape with a hole through the long axis of the X-ray detectable markers 105. The hole in the middle allows the radiation from the carrier body 110 to pass through the markers 105 so that the ends 108 and 109 will also emit radiation. In many instances, the ends 108 and 109 tend to be thicker than other parts of the housing 102 since the ends have to be welded after the carrier body 110 and the X-ray detectable markers 105 are inserted into the cavity 104. Consequently, less radiation may pass through the ends 108 and 109. By having substantially cylindrical holes in the X-ray detectable markers 105, more radiation will be able to pass through the ends 108 and 109 to alleviate the problem stated above. In further embodiments, the X-ray detectable markers 105 can also be modified such that the markers will be able to slide over a single piece carrier body. In other words, the carrier body can be inserted into the hole of the markers so that the markers can be positioned over any part of the carrier body.

Figure 7A:
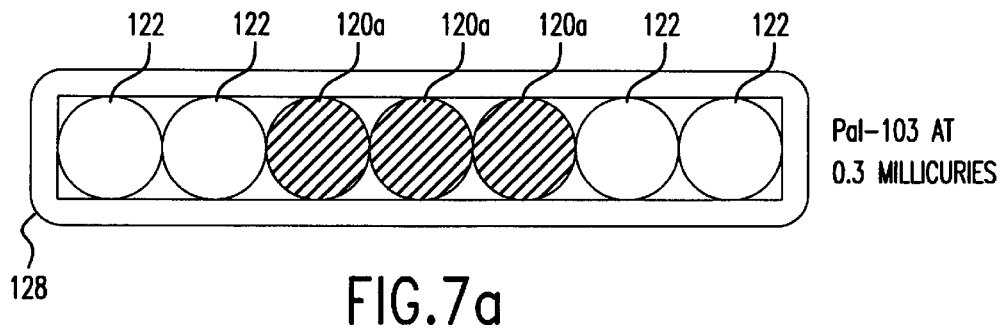
FIGS. 7a through 7d show cross-sectional views of radioactive seeds with different marker configurations to identify particular radioactive sources and dosage levels within the seeds.
Figure 7B:
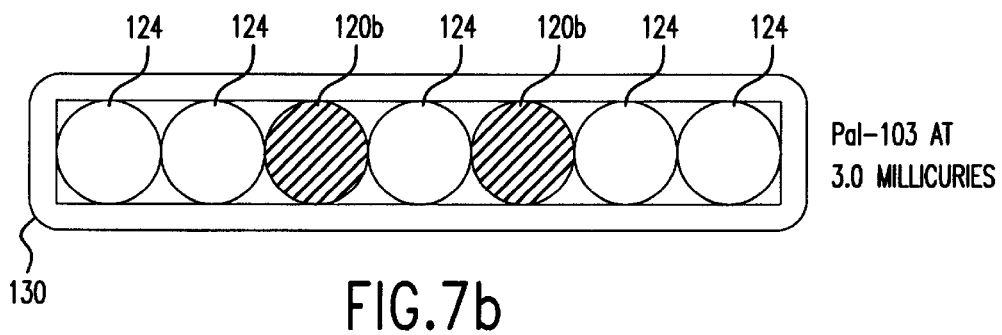

FIGS. 7a through 7d illustrate how different marker configurations within a radioactive seed can identify the type of radioactive sources in the seed and the dosage level of the seed. Each of the seeds 128, 130, 132 and 134 include at least two radioactive markers 120 in a particular configuration to identify the radioactive source in the seed and the dosage level. FIGS. 7a and 7b show cross-sections of seeds 128 and 130 having palladium-103 as a radioactive source in respective sets of carriers 122 and 124. Seed 128 includes three adjacent spherical X-ray markers 120a centered in the seed, leaving two radioactive carriers 122 on each side of the three X-ray markers 120a. In this embodiment, this particular configuration identifies the seed 128 as having palladium-103 as the radioactive source at a dosage of about 0.3 millicuries. Seed 130 has the same marker configuration of that of FIG. 7a except that the center X-ray marker 120a is replaced with a carrier 124. This particular configuration also identifies the source as palladium 103 but at a dosage of about 3.0 millicuries. The different marker configurations in seeds 128 and 130 are preferably detectable in X-ray imaging and allow the treating physician to distinguish the radioactive seeds implanted in the affected tissue region with the lower dosage from those implanted seeds having the higher dosage.

Figure 7C:
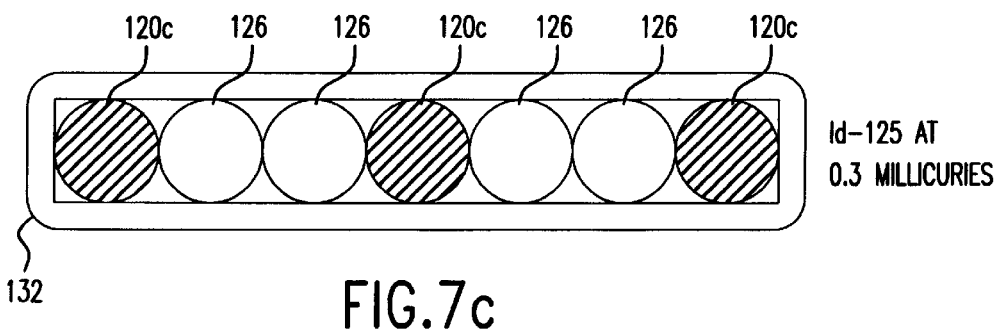
Figure 7D:
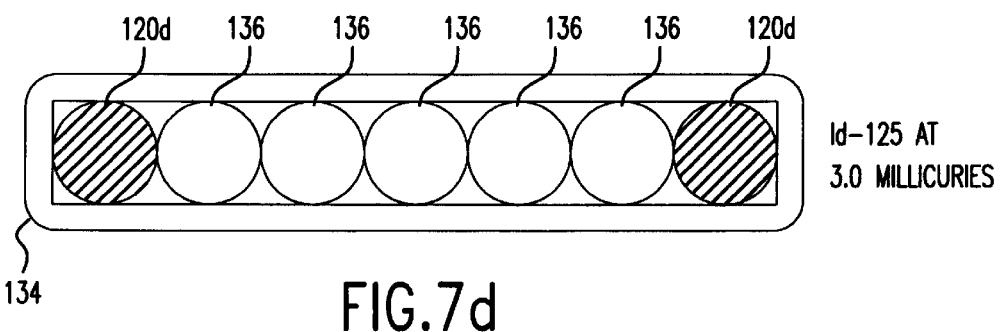

The radioactive seeds 132 and 134 of FIGS. 7c and 7d include respective sets of carriers 126 and 136 for providing an iodine-125 radioacive source. The radioactive seeds 132 and 134 also each include X-ray markers 120 at each opposite end of the respective radioactive seed. With X-ray imaging, the treating physician can distinguish those implanted radioactive seeds having radioactive markers at opposite ends of the seeds, corresponding with seeds having an iodine-125 source, from those seeds which do not have radioactive markers at opposite ends of the seeds, corresponding with seeds having a palladium-103 source. Also, in addition to having X-ray markers 120c at opposite ends of the capsule, the radioactive seed 132 also includes an X-ray marker 120c in the center of the capsule. The radioactive seed 134, on the other hand, does not include an X-ray marker in the center of the capsule. This allows the treating physician to distinguish implanted iodine-125 seeds having dosages of 0.3 millicuries, with the X-ray marker in the center of the capsule, from the implanted iodine-125 seeds having the 3.0 millicurie dosage, with no X-ray marker in the center of the seed.

The embodiments illustrated in FIGS. 7a through 7d enable the treating physician to better control and monitor the brachytherapy process in an affected tissue area by using different types of isotopes (e.g., iodine-125 or palladium-103) and using different levels of dosages in the radioactive seeds. This allows the treating physician to properly dose the core and periphery areas of the affected tissue. For example, a potential problem in prostrate brachytherapy is the overdosing of the core area with radiation and the under dosing of the periphery areas. The embodiments illustrated with reference to FIGS. 7a through 7d permit the accurate identification of the activity resulting from the implanted seeds at both the core and periphery areas using X-ray imaging to maintain proper dosage levels in the affected areas.

Accordingly, the placement of markers within the seed can assist in not only determining the orientation of seeds, but also differentiating among the different types of radioisotopes and levels of activity among particular implanted seeds. This is done by differentiating the different types of radioactive seeds using different X-ray marker configurations which are detectable using X-ray imaging. It is in this manner that the multiple markers in radioactive seeds as illustrated with reference to FIGS. 7a through 7d provide a previously unavailable system for monitoring the distribution of the activity of dosages in a patient's tissue during brachytherapy.

The radioactive seeds illustrated in FIGS. 7a through 7d having different radioisotopes and dosages may also be manufactured using a uniform manufacturing process. The process of manufacturing a radioactive seed for a particular radioisotope and a particular dosage is differentiated from the processes of the other types of radioactive seeds by the selection of appropriate carrier elements for the corresponding radio isotope and dosage level, and the placement of X-ray markers among the selected carrier elements within the capsule. This enables a single manufacturer to cost effectively provide the different types of radioactive seeds (i.e., having the particular radio isotope and dosage level) which are distinguishable using X-ray photography. Moreover, the treatment clinic can purchase the different radioactive seeds from a single vendor, simplifying a system employing different types of radioactive seeds at different dosage levels and radioisotope types. This offers distinct advantages over such a systems which would require the purchase of radioactive seeds from multiple manufacturers to provide differentiated radioactive seeds. With a system of seeds with multiple markers from a single manufacturer, such as those shown in FIGS. 7a through 7d, having X-ray detectable marker configurations indicative of the activity level or isotope type, the inconvenience of purchasing from multiple vendors is avoided.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A radioactive seed for use in radiation therapy, the radioactive seed comprising:

a sealed housing having an internal cavity;

at least one carrier body disposed within the cavity for maintaining a radioisotope, as a radiation source, in a distribution along a length of the cavity; and a plurality of X-ray detectable markers distributed along the length of the cavity, at least two of the X-ray detectable markers being laterally separated from one another by at least one carrier body, wherein the distribution of the plurality of X-ray markers reveals a seed treatment characteristic when the seed is exposed to an X-ray photography, said seed characteristic selected from the type of radioisotope maintained by the carrier body and the dosage level of the radioactive seed.

2. A radioactive seed for use in radiation therapy, the radioactive seed comprising:

a sealed container having a cavity;

a plurality of carriers substantially evenly distributed and laterally spaced along the length of the cavity, each of the plurality of carriers containing and maintaining a radioisotope as a radiation source; and a plurality of X-ray detectable markers distributed among the carriers such that the distribution of the markers discloses a seed treatment characteristic when the seed is exposed to X-ray photography, said seed treatment characteristic selected from the type of radioisotope maintained by the carrier body and the dosage level of the radioactive seed, wherein at least two of the X-ray detectable markers are laterally separated from one another by a carrier.

3. A system for providing radiation treatment to an affected tissue area, the system comprising:

a plurality of first radioactive seeds, each of the first radioactive seeds including:

a sealed housing having an internal cavity;

at least one carrier body disposed within the cavity for maintaining a radioisotope, as a radiation source, in a distribution along a length of the cavity; and a plurality of X-ray detectable markers distributed along the length of the cavity, at least two of the X-ray detectable markers being laterally separated from one another by at least one carrier body, and an implantation device to position the radioactive seeds in the affected tissue area, wherein the distribution of the plurality of X-ray markers in each radioactive seed reveals a seed treatment characteristic when the tissue area is exposed to X-ray photography, said seed treatment characteristic selected from the type of radioisotope maintained by the carrier body and the dosage level of the radioactive seed.

4. A radioactive seed for use in radiation therapy, the radioactive seed comprising:

a sealed housing having an internal cavity;

at least one carrier body disposed within the cavity for maintaining a radioisotope as a radiation source; and a plurality of X-ray detectable markers distributed within the cavity, wherein the distribution of the plurality of X-ray markers reveals a seed treatment characteristic when the seed is exposed to X-ray photography, said seed treatment characteristic selected from a type of radioisotope maintained by the carrier body and a dosage level of the radioactive seed.

5. A system for providing radiation treatment to an affected tissue area, the system comprising:

a plurality of radioactive seeds, each of the radioactive seeds including:

a sealed housing having an internal cavity;

at least one carrier body disposed within the cavity for maintaining a radioisotope as a radiation source; and a plurality of X-ray detectable markers distributed within the cavity, and an implantation device to position the radioactive seeds in the affected tissue area, wherein the distribution of the plurality of X-ray markers in each radioactive seed reveals a seed treatment characteristic when the tissue area is exposed to X-ray photography, said seed treatment characteristic selected from a type of radioisotope maintained by the carrier body and a dosage level of the radioactive seed.

* * * * *